United States Patent
Zhou et al.

(10) Patent No.: US 7,638,636 B2
(45) Date of Patent: Dec. 29, 2009

(54) PHOSPHONIUM AND IMIDAZOLIUM SALTS AND METHODS OF THEIR PREPARATION

(75) Inventors: Yuehui Zhou, Toronto (CA); Allan J. Robertson, Thorold (CA); John H. Hillhouse, Niagara Falls (CA); Douglas Baumann, St. Catharines (CA)

(73) Assignee: Cytec Technology Corp., Wilmington, DE (US)

( * ) Notice: Subject to any disclaimer, the term of this patent is extended or adjusted under 35 U.S.C. 154(b) by 592 days.

(21) Appl. No.: 10/521,973

(22) PCT Filed: Aug. 8, 2003

(86) PCT No.: PCT/CA03/01189

§ 371 (c)(1),
(2), (4) Date: Jul. 18, 2006

(87) PCT Pub. No.: WO2004/016631

PCT Pub. Date: Feb. 26, 2004

(65) Prior Publication Data

US 2006/0264645 A1 Nov. 23, 2006

(30) Foreign Application Priority Data

Aug. 16, 2002 (CA) .................... 2398682

(51) Int. Cl.
*C07D 233/00* (2006.01)
(52) U.S. Cl. ................. 548/335.1
(58) Field of Classification Search .............. 548/335.1; 558/203
See application file for complete search history.

(56) References Cited

U.S. PATENT DOCUMENTS 3,976,566 A 8/1976 Petrovich (Continued)

FOREIGN PATENT DOCUMENTS

EP 029003 A 10/1980

(Continued)

OTHER PUBLICATIONS

Wasserscheid et al., 2002, CAS: 136:200188.*
Holbrey et al., 2002. CAS: 138:338049.*
Wasserscheid et al., 2002, CAS:140:78757.*
Ludley, P. et al., Phosphonium tosylates as solvents for the Diels-Alder reaction; Tetrahedron Letters, vol. 42, No. 10, Mar. 4, 2001, pp. 2011-2014.
Comyns, C. et al., Clean catalysis with clean solvents—phosphonium tosylates for transfer hydrogenation reactions, Catalysis Letters, vol. 67, No. 2-4, Mar. 10, 2000, pp. 113-115.
Karodia, N. et al., Clean catalysis with ionic solvents—phosphonium tosylates for hydroformylation, Chemical Communications, No. 21, 1998, pp. 2341-2342.
Boy Cornils and Wolfgang A. Hermann, Aqueous Phase Organometallic Catalysis, Concepts and Applications, May 28, 2008, pp. 555-563.
Abdallah, D. J. et al., Smetic Liquid-Crystalline Phases of Quaternary Group VA (Especially Phosphonium) Salts with Three Equivalent Long n-Alkyl Chains. How Do Layered Assemblies Form in Liquid-Crystalline Phases?, Journal of the American Chemical Society, vol. 122, No. 13, Apr. 5, 2000, pp. 3053-3062.
Esteruelas, M. A. et al., Reductive Elimination of [Ph2C=C=CHPR3]BF4 from the Rhodium (III)—Allenyl Derivatives [Rh(acac){CH=C=CPh2}(PR3)2]BF4 (PR3 +PCy3, PiPR3), Organometallics, vol. 16, No. 21, Oct. 14, 1997, pp. 4572-4580.
Imrie, C. et al., Photolysis of (Arylmethyl) triphenylphosphonium Salts. Substituent, Counterion, and Solvent Effects on Reaction Products, Journal of Organic Chemistry, vol. 58, No. 21, 1993, pp. 5643-5649.

(Continued)

Primary Examiner—Rei-tsang Shiao
(74) Attorney, Agent, or Firm—Charles E. Bell

(57) ABSTRACT

Novel phosphonium and imidazolium salts and methods for preparing them are disclosed. The novel phosphonium and imidazolium compounds are useful as polar solvents and have the general formula (I): $Q^+X^-$ wherein $Q^+$ is formula (a) or formula (b); and $X^-$ is formula (c), formula (d) or formula (e); and wherein: each of $R^1$, $R^2$, $R^3$, $R^4$, $R^5$, $R^9$, $R^{10}$, $R^{11}$, $R^{12}$, and $R^{13}$ is independently a hydrocarbyl group; each of $R^6$, $R^7$, and $R^8$ is independently a hydrogen or hydrocarbyl group.

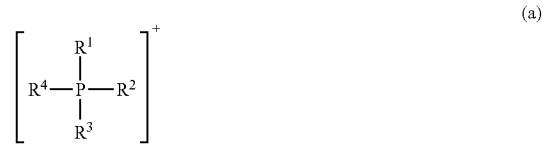

(a)

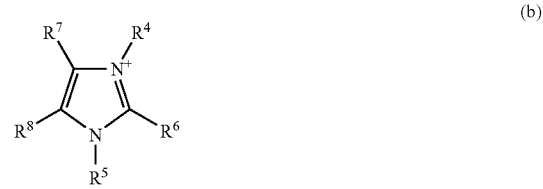

(b)

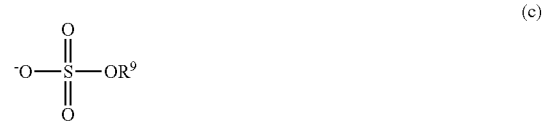

(c)

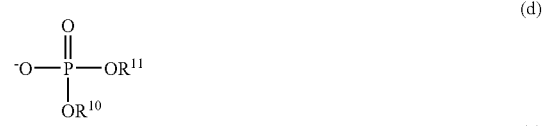

(d)

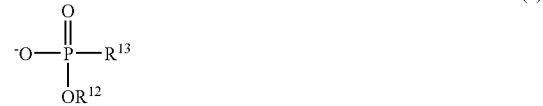

(e)

13 Claims, No Drawings

U.S. PATENT DOCUMENTS

| | | | | |
|---|---|---|---|---|
| 4,017,610 | A | 4/1977 | Baker | 514/107 |
| 4,837,394 | A | 6/1989 | Alexandrovich et al. | |
| 4,867,790 | A | 9/1989 | Jochum et al. | |
| 2004/0106823 | A1 | 6/2004 | Robertson et al. | 562/8 |
| 2006/0264645 | A1 | 11/2006 | Zhou et al. | 548/335.1 |

FOREIGN PATENT DOCUMENTS

| | | |
|---|---|---|
| EP | 0149480 A | 1/1985 |
| EP | 0161128 A | 11/1985 |
| EP | 0455257 A | 11/1991 |
| EP | 0640646 A1 | 3/1995 |
| EP | 0675130 B | 10/1995 |
| EP | 0895997 B | 2/1999 |
| EP | 1182197 A | 8/2000 |
| EP | 1182197 | 2/2002 |
| JP | 63119490 | 11/1986 |
| JP | 63119490 A | 5/1988 |
| WO | PCT/US96/19034 | 12/1995 |
| WO | WO97/23490 | 7/1997 |
| WO | PCT/GB99/03150 | 9/1998 |
| WO | 0016902 | 3/2000 |
| WO | PCT/US01/12780 | 4/2001 |
| WO | 0187900 | 11/2001 |
| WO | WO 02/079212 A | 10/2002 |
| WO | PCT/CA02/01919 | 12/2002 |
| WO | WO03/020843 | 3/2003 |
| WO | WO03/051894 | 6/2003 |
| WO | WO2004094438 A1 | 11/2004 |

OTHER PUBLICATIONS

Kanazawa, A. et al., Polymeric Phosphonium Salts as a Novel Class of Cationic Biocides. II. Effects of Counter Anion and Molecular Weight on Antibacterial Activity of Polymeric Phosphonium Salts, Journal of Polymer Science, Part A: Polymer Chemistry, vol. 31, No. 6, 1993, pp. 1441-1447.

Dema, A. et al., Transformation of Alkynylphosphine Oxides and Alkynylphosphonium Cations to 2-Alkylidene-1, 2-dihydro-3-phosphete Ligands by Pt-H Addition and Rearrangement Reactions, Organometallics, vol. 10, No. 4, 1991, pp. 1197-1200.

Jones, R. A. et al., Synthesis and X-ray Crystal Structure of (Triphenylmethyl) trimethylphosphonium Tetrafluoroborate, Journal of the Chemical Society, Perkin Transactions II, No. 1, 1980, pp. 117-120.

Cerichelli G., et al., Role of Counterions in the Catalytic Activity and Phase Equilibria of Phosphonium Salts in Water, Langmuir, vol. 16, No. 1, Jan. 11, 2000, pp. 156-171.

Albanese, D. et al., Synthesis of Pentacoordinated Tetraalkylammonium and Tetraalkylphosphonium Difluorosilicates, Tetrahedron Letters, vol. 36, No. 48, Nov. 27, 1995, pp. 8865-8866.

Masatsugu, O. et al., Effects of Crosslinking on Physical Properties of Phenol-Formaldehyde Novolac Cured Epoxy Resins, Journal of Applied Polymer Science, vol. 48, No. 4, Apr. 20, 1993, pp. 583-601.

Yanmaele, L., Non-polymeric Phosphonium Nordanting Agents, Research Disclosure, No. 287, 1988, pp. 133-134.

Barraud A. et al., A Novel Highly Conducting Phosphonium Tetracyanoquinodimethane Langmuir-Blodgett Film, vol. 160, No. 1, Jun. 1, 1988, pp. 81-85.

Adams, C. et al., Friedel-Crafts reactions in room temperature ionic liquids, Chemical Communications, No. 19, 1998, pp. 2097-2098.

Chauvin, Y. et al., Catalytic Dimerization of Alkenes by Nickle Complexes in Organochloroaluminate Molten Salts, Journal of the Chemical Society, Chemical Communications, No. 23, 1990, pp. 1715-1716.

Bohm, V. et al., Nonaqueous Ionic Liquids: Superior Reaction Media for the Catalytic Heck-Vinylation of Chloroarenes, Chemistry—A European Journal, vol. 6, No. 6, Mar. 17, 2000, pp. 1017-1025.

Chauvin, Y. et al., Catalytic Dimerization of Olefins by Nickle Complexes in Organochloroaluminate Molten Salts, vol. 90, No. 17, 1990, pp. 822-832.

Chauvin, Y. et al., Oligomerization of n-Butenes Catalyzed by Nickle Complexes Dissolved in Organochloroaluminate Ionic Liquids, Journal of Catalysis, vol. 165, 1997, pp. 275-278.

Fischer, T. et al., Diels-Alder Reactions in Room-Temperature Ionic Liquids, Tetrahedron Letters, vol. 40, No. 4, Jan. 22, 1999, pp. 793-796.

Wessolowski, H. et al., Novel perfluoroalkenylphosphonates and iodoperfluoroalkenes from 3,3-bis (trifluoromethyl) -1,1,2,4,4,4-hexafluoro-1-butylene and nonafluoro-n-butoxy-1,1,2-trifluoroethylene, Journal of Fluorine Chemistry, vol. 80, No. 2, 1996, pp. 149-152.

Sarbu, T. et al, ATRP of Methyl Methacrylatein in the Presence of Ionic Liquids with Ferrous and Copious Anions, Maromol. Chem. Phys. 2001, 202, pp. 3379-3397.

Sarbu, T. et al., "ATRP of Methyl Methacrylate in the Presence of Ionic Liquids with Ferrous and Cuprous Anions," Maromol. Chem. Phys. 2001, 202, pp. 3379-3397.

Opposition papers and corresponding translation for EP1587813.

Office Action Summary of May 1, 2008 of copending U.S. Appl. No. 10/549,223.

Office Action Summary of Feb. 4, 2009 of copending U.S. Appl. No. 10/549,223.

ISR of International Application PCT/US2004/006961, 2004.

ISR of International Application PCT/CA03/01189, 2003.

Welton T: "Room-Temperature Ionic Liquids. Solvents for/synthesis and Catalysis," Chemiak Reviews, American Chemical Society, Easton, US, vol. 99, 1999, pp. 2071-2083.

IPRP of PCT/CA03/01189, 2003.

IPRP of PCT/US2004/006961, 2004.

Haskin, BA et al., From the Field of Organic Insectofungicides Thion-Thiol Isomerization of Quarternary Phosphonium O.O-Dialkyldithiophosphates, 1967.

* cited by examiner

PHOSPHONIUM AND IMIDAZOLIUM SALTS AND METHODS OF THEIR PREPARATION

CROSS REFERENCE TO RELATED APPLICATIONS

This application is a U.S. National Stage application claiming priority to International Application No. PCT/CA2003/001189 filed on Aug. 8, 2003.

FIELD OF THE INVENTION

The present invention relates to novel phosphonium and imidazolium salts, their methods of preparation and their use, for example, as polar solvents.

BACKGROUND OF THE INVENTION

Low melting or liquid phosphonium and imidazolium salts have found utility as polar solvents known as "ionic liquids". Ionic liquids provide an attractive alternative to traditional organic solvents for chemical reactions for many reasons. Ionics liquids display low vapour pressure which, for industrial purposes, is a very important feature. They are essentially non-volatile, a property that eliminates many of the containment problems typically encountered with traditional organic solvents. Since ionic liquids are often composed of poorly coordinating ions, they have the potential to provide a highly polar yet poorly coordinating solvent. Moreover, many of these solvents are immiscible with traditional organic solvents and therefore provide a non-aqueous polar alternative for use in two-phase systems. Because of their distinctive solvent characteristics, they can be used to bring unusual combinations of reagents into the same phase. A recent review of the properties and uses of ionic liquids is provided in an article entitled "Room-Temperature Ionic Liquids. Solvents for Synthesis and Catalysis," by Thomas Welton (Chem. Rev. 1999, 99, 2071-2083).

Ionic liquids provide solvents with a wide liquid range and a high degree of thermal stability. However, there remains a need for increasing the solvent options available to chemists by developing novel ionic liquids with distinctive physical and chemical properties.

Ionic liquids can be prepared by a two step process, comprising the steps of (a) reacting a nitrogen-containing compound (for example, imidazole) or a phosphorus-containing compound with an alkylhalide to obtain a quaternary nitrogen or phosphorus halide salt; and (b) exchanging the halide ion with a suitable anion (ion exchange or metathesis) to obtain a low-melting quaternary nitrogen or phosphorus salt. This process has several drawbacks. For example, the end-product can be contaminated with residual halide ion, which may interfere with the activity of halide-sensitive catalysts. For instance, halide ions such as chloride ions coordinate with group VII metals such as palladium and platinum. If an ionic liquid is to be used in an environment where halide ions are unacceptable, even at low levels, halide salts should not be used in the starting materials or a further process must be used which ensures removal of halide ions from the ionic liquid. Also, the two-step process is inconvenient, as the ion-exchange step produces salt or acid side-products that must be removed by washing with water.

SUMMARY OF THE INVENTION

The current invention provides novel ionic compounds that find utility as ionic liquids and methods of preparing these compounds. The novel ionic compounds can have a broad range of phosphonium or imidazolium cations and a broad range of sulfate, phosphate or phosphonate anions Thus, the current invention provides:

(1) a compound having the general formula (I):

$$Q^+X^-$$

wherein $Q^+$ is

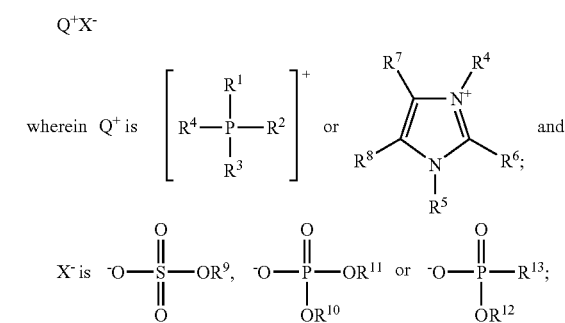

$X^-$ is $$\text{-O-}\overset{\overset{O}{\|}}{\underset{\|}{S}}\text{-OR}^9, \quad \text{-O-}\overset{\overset{O}{\|}}{\underset{|}{P}}\text{-OR}^{11} \quad \text{or} \quad \text{-O-}\overset{\overset{O}{\|}}{\underset{|}{P}}\text{-R}^{13};$$
$$\qquad\qquad\qquad\qquad OR^{10} \qquad\qquad OR^{12}$$

and wherein:

each of $R^1$, $R^2$, $R^3$, $R^4$, $R^5$, $R^9$, $R^{10}$, $R^{11}$, $R^{12}$ and $R^{13}$ is independently a hydrocarbyl group;

each of $R^6$, $R^7$, and $R^8$ is independently a hydrogen or hydrocarbyl group;

with the provisoes that:

(i) when $Q^+$ is a phosphonium cation and $X^-$ is a phosphate, or a phosphonate anion other than a phosphonate in which $R^{13}$ is perfluorohydrocarbyl, then $R^1$, $R^2$, $R^3$, and $R^4$ each has three or more carbon atoms;

(ii) when $Q^+$ is a phosphonium cation and $X^-$ is a sulfate then the sum of carbon atoms in $R^1$, $R^2$, $R^3$, and $R^4$ is greater than 4;

(iii) when $Q^+$ is an imidazolium cation, $X^-$ is not a sulfate anion; and (iv) when $Q^+$ is a phosphonium cation, $X^-$ is methylsulfate, and one of $R^1$, $R^2$, $R^3$ and $R^4$ is methyl, the other of $R^1$, $R^2$, $R^3$ and $R^4$ cannot all be 2-cyanoethyl.

In another aspect, the invention provides:

(1) a process for preparing a compound of formula (I), as defined above, wherein:

(a) a compound of formula (II):

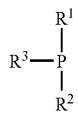

wherein each of $R^1$, $R^2$, and $R^3$ is defined as above, or formula (III):

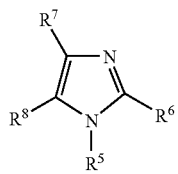

wherein each of $R^5$, $R^6$, $R^7$ and $R^8$ is defined as above, is reacted with:

(b) a compound defined by one of the following formulae:

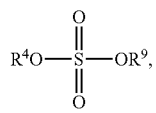

(IV)

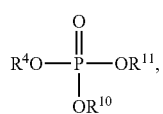

(V)

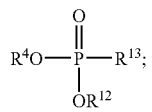

(VI)

wherein each of $R^4$, $R^9$, $R^{10}$, $R^{11}$, $R^{12}$ and $R^{13}$ is defined as above.

DESCRIPTION OF PREFERRED EMBODIMENTS

Suitable hydrocarbyl groups for $R^1$, $R^2$, $R^3$, $R^4$, $R^5$, $R^6$, $R^7$, $R^8$, $R^9$, $R^{10}$, $R^{11}$, $R^{12}$ and $R^{13}$ include: $C_1$-$C_{30}$ alkyl, $C_3$-$C_8$ cycloalkyl, $C_2$-$C_{30}$ alkenyl, $C_2$-$C_{30}$ alkynyl, $C_6$-$C_{11}$ aryl, or $C_7$-$C_{30}$ aralkyl, although hydrocarbyl groups with not more than 20 carbon atoms are preferred. It is noted that $R^{13}$ can also be a perfluoroalkyl group. It is possible for the groups $R^1$ to $R^{12}$, and $R^{13}$ when not perfluoroalkyl, to bear substituents, or to include heteroatoms, provided that the substituents or heteroatoms do not interfere with the preparation of the compounds of the invention, and do not adversely affect the desired properties of the compound. Acceptable substituents may include alkoxy, alkylthio, halo, carboxy, amino, acetyl, and hydroxyl groups, and heteroatoms that may be acceptable include nitrogen, oxygen and sulphur. Substituents are likely to increase the cost of the compounds of the invention and as the compounds are often used as solvents, they are used in such volume that cost is a significant factor. Hence, it is contemplated that, for the most part, substituents will not be present, although compounds in which $R^{13}$ is perfluoroinated hydrocarbyl constitute a preferred embodiment. If necessary, one of skill in the art can readily determine whether substituents or heteratoms of the hydrocarbyl groups interfere with preparation or desired properties of the compounds by routine experimentation that does not involve the exercise of any inventive faculty.

Preferred values for $R^1$, $R^2$, $R^3$, $R^4$, $R^5$, $R^6$, $R^7$, $R^8$, $R^9$, $R^{10}$, $R^{11}$, $R^{12}$ and $R^{13}$ include alkyl groups of 1 to 20 carbon atoms, for example, methyl, ethyl, propyl, isopropyl, n-butyl, isobutyl, n-pentyl, cyclopentyl, isopentyl, n-hexyl, cyclohexyl, (2,4,4'-trimethyl)pentyl, cyclooctyl, tetradecyl, etc. Alkyl groups of 3 to 10 carbon atoms are especially preferred values for $R^1$ to $R^{13}$.

For compounds containing a phosphonium cation, it is desired in some cases that $R^1$ to $R^4$ shall not be identical and preferably, that at least one of $R^1$ to $R^4$ shall contain a significantly higher number of carbon atoms than the others of $R^1$ to $R^4$. Phosphonium cations in which $R^1$ to $R^4$ are not identical are referred to as "asymmetric".

In some cases, it is preferred that at least one of $R^1$ to $R^{13}$ contains a higher number of carbon atoms, for example 14 or more. For example, the presence of one or more long alkyl chains may increase the ability of a phosphonium or imidazolium salt to dissolve nonpolar organic compounds.

In general, it is preferred that the salt of the current invention is a liquid below 100° C., more preferably below 50° C., and most preferably at or below room temperature. Preferred compounds, therefore, are those in which the particular groups $R^1$, $R^2$, $R^3$, $R^4$, $R^5$, $R^6$, $R^7$, $R^8$, $R^9$, $R^{10}$, $R^{11}$, $R^{12}$ and $R^{13}$, are selected to yield compounds that are liquid at room temperature. In general, increasing the total number of carbon atoms present in the hydrocarbyl groups $R^1$ to $R^{13}$ will tend to increase the melting point, although this effect can be counteracted somewhat by asymmetry and branching, and the tendency of sterically bulky ions to coordinate poorly. For example, steric bulk around the phosphorus atom or nitrogen atom of the cation or the sulfur atom or phosphorus atom of the anion will tend to decrease melting point of the salt and may be preferred. Therefore, more preferred are compounds wherein each of $R^9$, $R^{10}$, $R^{11}$, $R^{12}$, and $R^{13}$ and one or more of $R^1$, $R^2$, $R^3$, and $R^4$ or one or more of $R^4$, $R^5$, $R^6$, $R^7$, and $R^8$ has three or more carbon atoms. Also, branching of the hydrocarbyl groups $R^1$ to $R^{13}$ tends to decrease the melting point of the compound. Branching can occur at the alpha or omega carbon or at any intermediate point. In cases where the compound contains a phosphonium cation, the melting point tends to decrease as the degree of asymmetry around the phosphorus atom increases. For compounds containing an imidazolium cation, the melting melt will tend to decrease as the degree of symmetry in the imidazolium cation decreases.

For example, tetrabutylphosphonium dibutylphosphate is a solid at room temperature, but tri(iso-butyl)(n-butyl)phosphonium dibutylphosphate is a liquid at room temperature, despite the fact that both compounds have 24 carbon atoms.

Notably, certain compounds of formula (I) may have melting points below room temperature, below 0° C. and even below −20° C., in which case they may be suitable for use as solvents for reactions carried out at correspondingly low temperatures. For example, tetrabutylphosphonium butylsulfate remains a liquid at −20° C.

Compounds according to formula (I) that are hydrophobic or "water immiscible" are preferred for some purposes. The term "water immiscible" is intended to describe compounds that form a two phase system when mixed with water but does not exclude ionic liquids that dissolve in water nor ionic liquids that will dissolve water, provided that the two phase system forms. Compounds that have a large total number of carbons, equal to or greater than 20 and in particular greater than 25 or 26, or have at least one aryl group are more hydrophobic. Water immiscibility is a desirable feature of an ionic liquid not only because it renders the compound useful for biphasic reactions with an aqueous phase, but also because it facilitates purification and isolation of the ionic liquid when prepared according to certain methods. There is no critical upper limit on the total number of carbon atoms that may be present in a compound of formula (I). However, it is unlikely that the total will exceed 50.

Thus, the current invention contemplates compounds of formula (I) where properties may be modified by varying the values of the R groups present on either the anion or the cation. Selection of particular values for $R^1$ to $R^{13}$ to achieve particular melting points and degrees of water immiscibility is within the competence of a person skilled in the art, although it may require some routine experimentation.

Compounds according to formula (I) that have chirality provide a chiral environment for chemical reactions and may be especially preferred for certain purposes, such as a reaction having an assymetric or chiral transition state that may be stabilized by interaction with a suitable solvent. Examples of chiral compounds of formula (I) include compounds containing a phosphonium cation wherein $R^1$ to $R^4$ are all different or one of $R^1$ to $R^4$ is an enantiomer, such as 2,4,4'-trimethylpentyl, which group has one chiral atom.

Examples of preferred compound according to formula (I) include:

tri-(n-butyl)methylphosphonium methylsulfate;
tri-(n-butyl)ethylphosphonium ethylsulfate;
tetra-(n-butyl)phosphonium n-butylsulfate;
triethyl-(n-butyl)phosphonium n-butylsulfate;
tetrabutylphosphonium dibutylphosphate;
tri-iso-butyl-butylphosphonium dibutylphosphate
N,N-dimethylimidazolium dimethylphosphate;
N-methyl-N-butylimidazolium dibutylphosphate; and
N-methyl-N-ethylimidazolium ethylethanephosphonate;
and
tributylmethylphosphonium methyltrifluoromethanephosphonate.

In general, a phosphonium or imidazolium salt of formula (I) can be prepared by reacting a compound of formula (II) or formula (III), respectively, with one of the following: (1) a sulfate diester of formula (IV); (2) a phosphate triester of formula (V); or (3) a phosphonate diester of formula (VI).

In a preferred procedure for preparing compounds of formula (I), a tertiary phosphine of formula (II) or an imidazole of formula (III) is added directly to an ester (a sulfate diester, phosphate triester, or phosphonate diester), with stirring. The reaction is suitably carried out at an elevated temperature, for example in the range of 140° C. to 190° C., under an inert atmosphere.

The overall reaction is exothermic. Therefore, in order to control the temperature of the reaction mixture, it may be desirable to control the rate of addition in some cases and perhaps also to apply external cooling during the addition step. Since alkylphosphines may be pyrophoric, the addition of trialkylphosphine should also be controlled in order to avoid having a large amount of unreacted trialkylphosphine present in the reaction mixture, especially when the reaction is being carried out at elevated temperatures, for example over 100° C.

In general, the phosphine or imidazole and ester are present in the foregoing reaction in substantially stoichiometric amounts. In some cases, however, yields may be improved by using a slight molar excess of the phosphine or imidazole relative to the ester, for example in the range of 1.01 to 1.4 equivalents and preferably around 1.02 equivalents of the phosphine or imidazole.

Preferably, the reaction is carried out in the absence of solvent, in order to avoid a further step of purifying product away from solvent. However, the reaction may also be carried out in the presence of a solvent. In some cases, the presence of a solvent may be preferred as the solvent may enhance the rate at which the reaction proceeds.

The temperature of the reaction is not critical, although lower temperatures will result in longer reaction times. The reaction proceeds readily at elevated temperature, say up to 220° C., preferably in the range of 140-190° C., and is often complete in 8 hours at these temperatures. Certain alkylating agents, such as dimethyl-sulfate, are very active alkylating reagents and may be used for reactions carried out at room temperature. The initial step of adding the ester compound to the phosphine or imidazole, when required, may be conveniently carried out at room temperature.

The pressure of the reaction is not critical, and the reaction may be conveniently carried out at atmospheric pressure, preferably under an inert atmosphere, such as nitrogen. It is further preferable that the atmosphere be dry, in order to minimize the water content of the product.

If desired, any unreacted starting materials and/or residual water may be removed by, for example, drying under vacuum.

The foregoing process may be especially preferred if it is desirable to avoid contamination of end-product with halide ions or to avoid or minimize the amount of water contained in the end-product. However, compounds of formula (I) may be prepared by any suitable procedure.

The phosphonium and imidazolium salts of the current invention may be used as polar solvents for chemical reactions such as Michael additions, aryl coupling, Diels-Alder, alkylation, biphasic catalysis, Heck reactions, hydrogenation, or for enzymatic reactions, for example lipase reactions.

EXAMPLES

In the following examples, starting material phosphines are made by Cytec Canada, Inc. and their purity determined by gas chromatography (GC). N-methylimidazole and dibutylsulfate were purchased form Lancaster. The remaining starting materials were purchased from Aldrich and used as they were purchased. Structures were confirmed by 1H-NMR, $^{13}$C-NMR and $^{31}$P-NMR.

Example 1

Preparation of tri-(n-butyl)methylphosphonium methylsulfate

To a flask containing 132 g (99% pure, 1.036 mole) dimethylsulfate, at room temperature, tri(n-butyl)phosphine (218 g, 98% pure, 1.056 mole) was gradually added, over a period of three hours, with stirring under nitrogen. The temperature in the flask increased gradually to 100° C. during the addition.

When the addition was complete, the reaction mixture as heated to 150° C. for 8 hours, then dried in a rotary evaporator under 140° C./5 mm Hg for 5 hours.

Tri-(n-butyl)methylphosphonium methylsulfate product was obtained in 100% yield (348 g). NMR analysis was consistent with tri-(n-butyl)methylphosphonium methylsulfate. The product was a liquid at room temperature. $^1$H-NMR (CDCl$_3$, 300.13 MHz, δ): 3.46 (s, 3H, —OCH$_3$), 2.09 (m, 6H, 3×CH$_3$CH$_2$CH$_2$—CH$_2$—P$^+$), 1.71 (d, 3H, CH$_3$P$^+$), 1.32 (m, 12H, 3×CH$_3$—CH$_2$CH$_2$—CH$_2$P$^+$), 0.76 (m, 9H, 3×CH$_3$—CH$_2$CH$_2$CH$_2$P$^+$). $^{31}$P-NMR (CDCl$_3$, 81.015 MHz, δ): 27.00 (P$^+$).

Example 2 tri-(n-butyl)ethylphosphonium ethylsulfate

To a flask containing 100 g (98% pure, 0.636 mole) diethylsulfate, at 60° C., tri(n-butyl)phosphine (132 g, 98% pure, 0.638 mole) was added gradually, over a period of two hours, with stirring under nitrogen. The temperature in the flask increased slowly to 120° C. during the addition.

When the addition was complete, the reaction mixture was heated to 150° C. for 3 hours, then dried in a rotary evaporator under 160° C./5 mm Hg for 5 hours.

Tri-(n-butyl)ethylphosphonium ethylsulfate product was obtained in 100% yield (230 g). Analysis by NMR was consistent with tri-(n-butyl)ethylphosphonium ethylsulfate. The product was a liquid at room temperature. $^1$H-NMR (CDCl$_3$, 300.13 MHz, δ): 4.05 (q, 2H, —O—CH$_2$—CH$_3$), 2.34 (m, 6H, 3×CH$_3$CH$_2$CH$_2$—CH$_2$—P$^+$), 2.34 (m, 2H, CH$_3$—CH$_2$—P$^+$), 1.27 (m, 3H, CH$_3$—CH$_2$P$^+$), 1.27 (m, 3H, —OCH$_2$—CH$_3$), 0.97 (m, 9H, 3×CH$_3$—CH$_2$CH$_2$CH$_2$ P$^+$). $^{31}$P-NMR (CDCl$_3$, 81.015 MHz, δ): 35.05 (s, P$^+$).

Example 3 tetra-(n-butyl)phosphonium butylsulfate

To a flask containing: 50 g (95% pure, 0.226 mole) di-(n-butyl)sulfate, at 80° C., tri(n-butyl)phosphine (48 g, 98% pure, 0.233 mole) was gradually added, over a period of one hour, with stirring under nitrogen. The temperature in the flask increased gradually to 120° C. during the addition.

When the addition was complete, the reaction mixture was heated to 190° C. for 8 hours, then dried in a rotary evaporator under 160° C./5 mm Hg for 5 hours.

Tetra-(n-butyl)phosphonium n-butylsulfate product was obtained in 96% yield (90 g). Analysis by NMR was consistent with tetra-(n-butyl)phosphonium n-butylsulfate but indicated that the product contained some impurity. The product was a liquid at room temperature. $^1$H-NMR (CDCl$_3$, 300.13 MHz, δ): 3.77 (t, 2H, —OCH$_2$—CH$_2$CH$_3$), 2.09 (m, 8H, 4×CH$_3$CH$_2$CH$_2$—CH$_2$—P$^+$), 1.41 (qu, 2H, —OCH$_2$—CH$_2$—CH$_2$CH$_3$), 1.33 (m, 16H, 4×CH$_3$—CH$_2$CH$_2$—CH$_2$P$^+$), 1.19 (qu, 2H, —OCH$_2$CH$_2$—CH$_2$—CH$_3$), 0.76 (m, 12H, 4×CH$_3$—CH$_2$CH$_2$CH$_2$P$^+$), 0.76 (m, 3H, —OCH$_2$CH$_2$CH$_2$—CH$_3$). $^{31}$P-NMR (CDCl$_3$, 81.015 MHz, δ): 33.49.

Example 4

Synthesis of tri-ethyl(n-butyl)phosphonium butylsulfate

Triethylphosphine (7.2 g, 99%, 0.06 mol) was added dropwise to a 125 mL flask containing 12.6 (99%, 0.06 mol) di-n-butylsulfate at 80° C. under nitrogen and with stirring over a period of 75 minutes. The liquid was stirred at 140° C. for an additional 3.5 hours. The liquid was cooled, moved to a rotary evaporator and dried at 125° C./5 mm Hg for 6 hours. The product (16.73 g, yield 85%) was a wax-like solid at room temperature (m.p. from DSC measurement: 40.0° C.). $^1$H-NMR (CDCl$_3$, 300.13 MHz, δ): 3.98 (t, 2H, CH$_3$CH$_2$CH$_2$—CH$_2$—O—), 2.34 (m, 8H, 3×CH$_3$—CH$_2$P$^+$ and CH$_3$CH$_2$CH$_2$—CH$_2$P$^+$), 1.54 (m, 8H, CH$_3$—CH$_2$CH$_2$—CH$_2$O— and CH$_3$—CH$_2$CH$_2$—CH$_2$P$^+$), 1.25 (m, 3×CH$_3$—CH$_2$P$^+$), 0.91 (m, 6H, CH$_3$CH$_2$CH$_2$—CH$_2$O— and CH$_3$CH$_2$CH$_2$—CH$_2$P$^+$). $^{31}$P-NMR (CDCl$_3$, 81.015 MHz, δ): 38.88 (s, P$^+$).

Example 5

Synthesis of tetrabutylphosphonium dibutylphosphate

Tri-n-butylphosphine (215 g, 94%, 1.0 mole) was added dropwise over a period of 4 hours to a flask containing 272 g (98%, 1.0 mole) of tributylphosphate at 170° C. When the addition was complete, the reaction mixture was heated to 200° C. and stirred at this temperature for 24 hours. The viscous liquid was dried in a rotary evaporator at 160° C./5 mm Hg for 5 hours. The product (363 g, yield 77.5%) was pure according to NMR. At room temperature the product was a white, wax-like solid (m.p. from DSC measurement: 28.0° C.). $^1$H-NMR (CDCl$_3$, 300.13 MHz, δ): 3.84 (q, 4H, 2×CH$_3$CH$_2$CH$_2$—CH$_2$—O—), 2.38 (m, 8H, 4×CH$_3$CH$_2$CH$_2$—CH$_2$P$^+$), 1.53 (m, 16H, 4×CH$_3$—CH$_2$CH$_2$—CH$_2$P$^+$), 1.40 (m, 8H, 2×CH$_3$—CH$_2$CH$_2$—CH$_2$O—), 0.97 (m, 12H, 4×CH$_3$—CH$_2$CH$_2$CH$_2$P$^+$), 0.90 (m, 6H, 2×CH$_3$—CH$_2$CH$_2$CH$_2$O—). $^{31}$P-NMR (CDCl$_3$, 81.015 MHz, δ): 33.72 (P$^+$), 0.94 [m, (RO)$_2$—P(=O)—O$^-$].

Example 6

Synthesis of tri-iso-butyl-butylphosphonium dibutylphosphate

Tri-iso-butylphosphine (206.5 g, 98%, 1.0 mole) was added dropwise over a period of 2 hours to a flask containing 271.8 g (98%, 1.0 mole) of tributylphosphate at 200° C. under nitrogen and stirring. When the addition was complete, the mixture was stirred at the same temperature for an additional 15 hours. The mixture was cooled down and moved to a rotary evaporator and dried under 160° C./5 mm Hg for 5 hours. The product (320.7 g, yield 68.5%) was pure judged from NMR and liquid at room temperature. $^1$H-NMR (CDCl$_3$, 300.13 MHz, δ): 3.76 (q, 4H, 2×CH$_3$CH$_2$CH$_2$—CH$_2$O—), 2.19 (q, 6H, 3×CH$_3$ (CH$_3$)CH—CH$_2$P$^+$), 1.96 (m, 3H, 3×CH$_3$ (CH$_3$)CH—CH$_2$P$^+$), 1.96 (m, 2H, CH$_3$CH$_2$CH$_2$—CH$_2$P$^+$), 1.44 (m, 8H, CH$_3$—CH$_2$CH$_2$—CH$_2$O—), 1.24 (m, 4H, CH$_3$—CH$_2$CH$_2$—CH$_2$P$^+$), 1.01 (d, 18H, 3×CH$_3$CH(CH$_3$)—CH$_2$P$^+$), 0.84 (t, 3H, CH$_3$—CH$_2$CH$_2$CH$_2$P$^+$), 0.77 (t, 6H, 2×CH$_3$—CH$_2$CH$_2$CH$_2$O—). $^{31}$P-NMR (CDCl$_3$, 81.015 MHz, δ): 32.60 (P$^+$), −0.61 [d, (RO)$_2$—P(=O)—O$^-$].

Example 7

Synthesis of N,N-dimethylimidazolium dimethylphosphate

Trimethylphosphate (127.6 g, 0.883 mole) was added dropwise over a period of 1 hour to a 300 ml flask containing 72.2 g (99%, 0.87 mole) N-methylimidazole at room temperature. The temperature of the reaction mixture was slowly increased to 140° C. As the reaction mixture approached 140° C., there was an acceleration in the rate at which the temperature increased. The reaction mixture was stirred at the same temperature for an additional 3 hours. The mixture was cooled and moved to a rotary evaporator and dried at 150° C./5 mm Hg for 4 hours. The product (194 g, yield 100%) was pure, judged from NMR and liquid at room temperature. $^1$H-NMR (CDCl$_3$, 300.13 MHz, δ): 10.40 (s, 1H, —N—CH=N—), 7.43 (s, 2H, —N—CH=CH—N—), 3.91 (s, 6H, N—CH$_3$), 3.46 (d, 6H, —OCH$_3$). $^{31}$P-NMR (CDCl$_3$, 81.015 MHz, δ): 3.01 [s, (RO)$_2$—P(=O)—O$^-$].

Example 8

Synthesis of N-methyl-N-butylimidazolium dibutylphosphate

Tributylphosphate (137.2 g, 0.505 mole) was added dropwise, slowly, to a 300 ml flask containing 41.5 g (99%, 0.5 mole) N-methylimidazole at 170° C. under nitrogen and stirring. The liquid was stirred at the same temperature for an additional 5 hours. The liquid was cooled and moved to a rotary evaporator and dried at 150° C./5 mm Hg for 4 hours. The product (171.3 g, yield 98%) was pure, as judged from NMR, and was liquid at room temperature. $^1$H-NMR (CDCl$_3$, 300.13 MHz, δ): 10.37 (s, 1H, —N—CH=N—), 7.50 (s, 1H, —N—CH=CH—N—), 7.29)s, 1H, —N—CH=CH—N—), 4.09 (t, 2H, —N—CH$_2$—CH$_2$CH$_2$CH$_3$), 3.87 (s, 3H, —N—CH$_3$), 3.67 (m, 4H, —O—CH$_2$—CH$_2$CH$_2$CH$_3$), 1.67 (qu, 2H, —NCH$_2$—CH$_2$—CH$_2$CH$_3$), 1.40 (m, 4H, 2×—OCH$_2$—CH$_2$—CH$_2$CH$_3$), 1.16 (m, 4H, —OCH$_2$CH$_2$—

CH$_2$—CH$_3$), 1.16 (m, 2H, —NCH$_2$CH$_2$—CH$_2$CH$_3$), 0.70 (m, 6H, 2×—OCH$_2$CH$_2$CH$_2$—CH$_3$), 0.70 (m, 3H, —NCH$_2$CH$_2$CH$_2$—CH$_3$). $^{31}$P-NMR (CDCl$_3$, 81.015 MHz, δ): 0.95 [s, (RO)$_2$—P(=O)—O$^-$].

Example 9

Synthesis of N-methyl-N-ethylimidazolium ethylethanephosphonate

Diethylethanephosphonate (68.2 g, 99%, 0.406 mole) was dripped into a 300 ml flask containing 33.3 g (99%, 0.402 mole) N-methylimidazole at 160° C. under nitrogen and stirring over a period of 80 minutes. The liquid was stirred at the same temperature for an additional 10 hours. The liquid was cooled, moved to a rotary evaporator and dried at 140° C./5 mmHg for 2.5 hours. The product (92.4 g, yield 92%) was a liquid at room temperature. $^1$H-NMR (CDCl$_3$, 300.13 MHz, δ): 10.99 (s, 1H, —N—CH=N—), 7.73 (s, 1H, —N—CH=CH—N—), 7.65 (s, 1H, —N—CH=CH—N—), 4.39 (q, 2H, —N—CH$_2$—CH$_3$), 4.09 (s, 3H, —NCH$_3$), 3.92 (m, 2H, —O—CH$_2$—CH$_3$), 1.56 (m, 3H, —OCH$_2$—CH$_3$), 1.56 (m, 2H, —(O=)P—CH$_2$—CH$_3$), 1.19 (m, 3H, —(O=)PCH$_2$—CH$_3$), 1.19 (m, 3H, —NCH$_2$—CH$_3$). $^{31}$P-NMR (CDCl$_3$, 81.015 MHz, δ): 25.57 [s, RO—(R)P(=O)—O$^-$].

Example 10 tetraalkylphosphonium alkyl alkanephosphonate

Tetraalkylphosphonium alkyl alkanephosphonate compounds can be made by reacting a trialkylphosphine with a dialkyl alkanephosphonate according to the process described in Example 1 except that dialkyl alkane phosphonate is used in place of dimethylsulfate.

Dialkyl alkanephosphonates which are used as starting materials can be made according to the Michaelis-Arbuzov reaction:

(RO)$_3$P+R'CH$_2$X→(RO)$_2$P(=O)CH$_2$R'+RX

Typical Michaelis-Arbuzov reactions and conditions for carrying out the reactions are described in a review article by A. K. Bhattacharya, G. Thyagarajan, Chemical Review, 1981, volume 81, page 415 the contents of which are herein incorporated by reference. Michaelis-Arbuzov reactions specifically for making dialkyl fluorinated alkanephosphonates, as exemplified by the synthesis of diethyl trifluoromethanephosphonate, are described in: T. Mahmood, J. M. Shreeve, *Synthesis Communications*, 1987, 17(1), 71-75, (the contents of which are herein incorporated by reference) and in D. J. Burton, R. M. Flynn, *Synthesis*, 1979, 615. In addition, V. I. Shibaev, A. V. Garabadzhiu, A. A. Rodin, Zh. *Obshch. Khim.* 1983, 53(8), 1743-1745 (the contents of which are herein incorporated by reference) describes a method for synthesizing di(isobutyl)trifluoromethanephosphonate.

By way of illustration, in a typical reaction, one equivalence of the alkylhalide R'CH$_2$X is added slowly into a flask containing 1.3-2 equivalence of trialkylphosphite (RO)$_3$P through an addition funnel under stirring. The excess of the trialkylphosphite can serve as solvent for the reaction. The reaction may be carried out over a range of temperatures, for example in the range of room temperature to 150° C. Preferably, the reaction is carried out at a temperature below the boiling points of the starting materials. The boiling point of trimethylphosphite is 112° C., triethylphosphite is 155° C. If an elevated reaction temperature is preferred, the trialkylphosphite in the flask can be preheated to that temperature. After all material has been added the flask, the reaction mixture can be refluxed for a suitable period of time, typically several hours. Any remaining unreacted trialkylphosphite and the byproduct alkylhalide R'X of the reaction can be removed by evaporating the mixture under vacuum.

The foregoing reaction may be used to make partially and completely fluorinated alkane phosphonates for use in making salts of formula (I). For example, when a compound represented by the general formulae C$_n$F$_{2n+1}$I is used as the alkyl halide in the foregoing reaction, the resulting Michaelis-Arbuzov phosphonate is a dialkyl perfluoroalkanephosphonate. When reacted with a trialkylphosphine, the resulting phosphonium salt is a tetraalkylphosphonium alkyl perfluoroalkanephosphonate, which compounds may be especially preferred for some applications, such as two-phase reactions where one phase is aqueous and the ionic liquid phase is necessarily hydrophobic.

The invention claimed is:

1. A compound having the general formula (I):

Q$^+$X$^-$

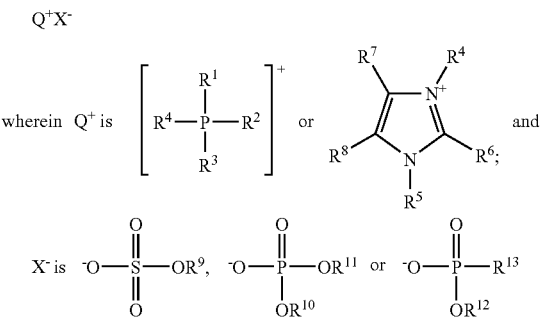

and wherein:
each of R$^1$, R$^2$, R$^3$, R$^4$, R$^5$, R$^9$, R$^{10}$, R$^{11}$, R$^{12}$ and R$^{13}$ is independently a hydrocarbyl group;
each of R$^6$, R$^7$ and R$^8$ is independently a hydrogen or a hydrocarbyl group; with the provisoes that:
(i) when Q$^+$ is a phosphonium cation and X$^-$ is a phosphate, or a phosphonate anion other than a phosphonate in which R$^{13}$ is perfluorohydrocarbyl, then R$^1$, R$^2$, R$^3$, and R$^4$ each has three or more carbon atoms;
(ii) when Q$^+$ is a phosphonium cation and X$^-$ is an alkylsulfate then the sum of carbon atoms in R$^1$, R$^2$, R$^3$, and R$^4$ is greater than 4;
(iii) when Q$^+$ is an imidazolium cation, X$^-$ is not an alkylsulfate anion;
(iv) when Q$^+$ is a phosphonium cation, X$^-$ is methylsulfate, and one of R$^1$, R$^2$, R$^3$, and R$^4$ is methyl, the others of R$^1$, R$^2$, R$^3$, and R$^4$ cannot be 2-cyanoethyl; and
(v) Q$^+$X$^-$ is not 1-butyl-3-methylimidazolium dibutylphosphate.

2. A compound according to claim 1, wherein Q$^+$ is a tetralkylphosphonium and X$^-$ is an alkylsulfate anion.

3. A compound according to claim 2, wherein R$^1$, R$^2$, and R$^3$ are hydrocarbyl groups with three or more carbon atoms.

4. A compound according to claim 2, wherein R$^1$, R$^2$, and R$^3$ are each n-butyl.

5. A compound according to claim 1, wherein:
R$^4$ is methyl and R$^5$ is methyl; or
R$^4$ is ethyl and R$^5$ is ethyl; or
R$^4$ is n-butyl and R$^5$ is n-butyl.

6. A compound according to claim 1, wherein the compound is selected from the group consisting of tri-(n-butyl)methylphosphonium methylsulfate;
tri-(n-butyl)ethylphosphonium ethylsulfate;
tetra-(n-butyl)phosphonium n-butylsulfate;
triethyl-(n-butyl)phosphonium n-butylsulfate;
tetrabutylphosphonium dibutylphosphate;
tri-iso-butyl-butylphosphonium dibutylphosphate;
N,N-dimethylimidazolium dimethylphosphate;
N-methyl-N-ethylimidazolium ethylethanephosphonate; and
tributylmethylphosphonium methyltrifluoromethanephosphonate.

7. A process for preparing a compound of formula (I):

$$Q^+X^-$$

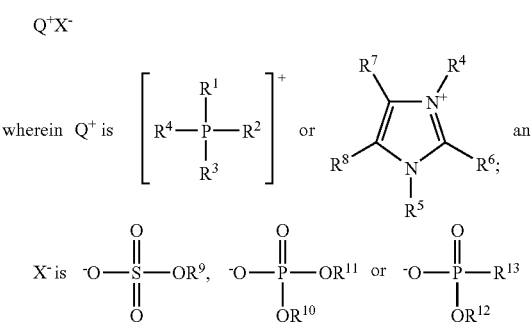

and wherein:
- each of $R^1$, $R^2$, $R^3$, $R^4$, $R^5$, $R^9$, $R^{10}$, $R^{11}$, $R^{12}$, and $R^{13}$ is independently a hydrocarbyl group;
- each of $R^6$, $R^7$, and $R^8$, is a hydrogen or hydrocarbyl group;

with the provisoes that:
(i) when $Q^+$ is a phosphonium cation and $X^-$ is a phosphate, or a phosphonate anion other than a phosphonate in which $R^{13}$ is perfluorohydrocarbyl, then $R^1$, $R^2$, $R^3$, and $R^4$ each has three or more carbon atoms;
(ii) when $Q^+$ is a phosphonium cation and $X^-$ an alkylsulfate then the sum of carbon atoms in $R^1$, $R^2$, $R^3$, and $R^4$ is greater than 4;
(iii) when $Q^+$ is an imidazolium cation, $X^-$ is not an alkylsulfate;
(iv) when $Q^+$ is a phosphonium cation, $X^-$ is methylsulfate, and one of $R^1$, $R^2$, $R^3$, and $R^4$ is methyl, the others of $R^1$, $R^2$, $R^3$, and $R^4$ cannot be 2-cyanoethyl; and
(v) $Q^+X^-$ is not 1-butyl-3-methylimidazolium dibutylphosphate the process comprising reacting a compound of formula (II):

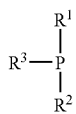

wherein each of $R^1$, $R^2$, and $R^3$ is independently a hydrocarbyl group, or formula (III):

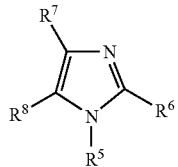

wherein $R^5$ is a hydrocarbyl group, and cation of $R^6$, $R^7$ and $R^8$ is independently a hydrogen or hydrocarbyl group, with a compound defined by one of the following formulae:

           (IV)

           (V)

           (VI)

wherein each of $R^4$, $R^9$, $R^{10}$, $R^{11}$, $R^{12}$ and $R^{13}$ is a hydrocarbyl group.

8. The process of claim 7, wherein the reaction is carried out in the absence of solvent.

9. The process of claim 7, wherein $Q^+$ is a tetralkylphosphonium and $X^-$ is an alkylsulfate anion.

10. The process of claim 9, wherein $R^1$, $R^2$, and $R^3$ are hydrocarbyl groups with three or more carbon atoms.

11. The process of claim 9, wherein $R^1$, $R^2$, and $R^3$ are each n-butyl.

12. The process of any one of claims 7 to 8, wherein
(a) $R^4$ and $R^5$ are both methyl; or
(b) $R^4$ and $R^5$ are both ethyl; or
(c) $R^4$ and $R^5$ are both n-butyl.

13. The process of claim 7 or 8, wherein the compound of formula (I) is selected from the group consisting of
tri-(n-butyl)methylphosphonium methylsulfate;
tri-(n-butyl)ethylphosphonium ethylsulfate;
tetra-(n-butyl)phosphonium n-butylsulfate;
triethyl-(n-butyl)phosphonium n-butylsulfate;
tetrabutylphosphonium dibutylphosphate;
tri-iso-butyl-butylphosphonium dibutylphosphate
N,N-dimethylimidazolium dimethylphosphate;
N-methyl-N-ethylimidazolium ethylethanephosphonate; and
tributylmethylphosphonium methyltrifluoromethanephosphonate.

* * * * *

UNITED STATES PATENT AND TRADEMARK OFFICE
CERTIFICATE OF CORRECTION

PATENT NO. : 7,638,636 B2 Page 1 of 1
APPLICATION NO. : 10/521973
DATED : December 29, 2009
INVENTOR(S) : Zhou et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 743 days.

Signed and Sealed this

Ninth Day of November, 2010

David J. Kappos
*Director of the United States Patent and Trademark Office*